United States Patent
Zhou et al.

(10) Patent No.: US 12,258,330 B2
(45) Date of Patent: Mar. 25, 2025

(54) METHOD FOR PREPARING VORICONAZOLE AND INTERMEDIATE THEREOF

(71) Applicants: Zhejiang Huahai Pharmaceutical Co., Ltd., Xunqiao (CN); Zhejiang Huahai LiCheng Pharmaceutical Co., Ltd., Xunqiao (CN)

(72) Inventors: Wenxiang Zhou, Xunqiao (CN); Wenfeng Huang, Xunqiao (CN); Jiaxing Hu, Xunqiao (CN)

(73) Assignees: Zhejiang Huahai Pharmaceutical Co., Ltd., Xunqiao (CN); Zhejiang Huahai LiCheng Pharmaceutical Co., Ltd., Xunqiao (CN)

( * ) Notice: Subject to any disclaimer, the term of this patent is extended or adjusted under 35 U.S.C. 154(b) by 895 days.

(21) Appl. No.: 17/430,794

(22) PCT Filed: Feb. 18, 2020

(86) PCT No.: PCT/CN2020/075707
§ 371 (c)(1),
(2) Date: Aug. 13, 2021

(87) PCT Pub. No.: WO2020/169025
PCT Pub. Date: Aug. 27, 2020

(65) Prior Publication Data
US 2022/0162189 A1 May 26, 2022

(30) Foreign Application Priority Data
Feb. 19, 2019 (CN) .......................... 201910121961.0

(51) Int. Cl.
C07D 403/06 (2006.01)
(52) U.S. Cl.
CPC ................. *C07D 403/06* (2013.01)
(58) Field of Classification Search
CPC .................................................. C07D 403/06
See application file for complete search history.

(56) References Cited

U.S. PATENT DOCUMENTS

2019/0002440 A1* 1/2019 Huang ................ C07D 403/06

FOREIGN PATENT DOCUMENTS

| CN | 1195346 A | | 10/1998 | | |
|---|---|---|---|---|---|
| CN | 102190628 A | | 9/2011 | | |
| CN | 105503834 A | | 4/2016 | | |
| CN | 103788073 A | * | 11/2017 | ........... | C07D 403/06 |
| CN | 107827876 A | | 3/2018 | | |
| CN | 106117186 A | * | 8/2018 | ........... | C07D 249/08 |

OTHER PUBLICATIONS

Extended European Search Report for EP 20758561.3 mailed Nov. 11, 2021 (7 pages).
Andrea I. H. Adams et al., "LC Stability Studies of Voriconazole and Structural Elucidation of Its Major Degradation Product", Chromatographia, vol. 69, p. S115-S122, Apr. 1, 2009.
International Search Report (ISR) for PCT/CN2020/075707 mailed Apr. 29, 2020 (5 pages).
Wirittten Opinion (WO) for PCT/CN2020/075707 mailed Apr. 29, 2020 (11 pages).

* cited by examiner

Primary Examiner — Joseph K McKane
Assistant Examiner — Jalisa Holmes Ferguson
(74) Attorney, Agent, or Firm — Shumaker, Loop & Kendrick, LLP

(57) ABSTRACT

Disclosed is a method for preparing voriconazole and an intermediate thereof. In the method, a voriconazole condensate isomer is reacted as a starting material in the presence of an acid to obtain 4-chloro-6-ethyl-5-fluoropyrimidine and 2',4'-difluoro-2-[1-(1H-1,2,4-triazolyl)]acetophenone. A method for preparing voriconazole by using the intermediate thus obtained is further disclosed. By adopting the method of the present invention, the utilization rate of starting materials and auxiliary materials for preparing voriconazole on the basis of the prior art can be greatly improved, thereby reducing costs.

15 Claims, No Drawings

METHOD FOR PREPARING VORICONAZOLE AND INTERMEDIATE THEREOF

This application claims the priority of China Patent Application No. 201910121961.0, filed before the Chinese Patent Office on Feb. 19, 2019, titled METHOD FOR PREPARING VORICONAZOLE AND INTERMEDIATE THEREOF; which is hereby incorporated by reference in its entirety.

FIELD OF THE INVENTION

The present invention relates to a method for preparing voriconazole and an intermediate thereof, which belongs to the field of medical technology.

BACKGROUND OF THE INVENTION

The chemical name of voriconazole is (2R,3S)-2-(2,4-difluorophenyl)-3-(5-fluoro-4-pyrimidinyl)-1-(1H-1,2,4-triazol-1-yl)-2-butanol, and its chemical formula is as follows:

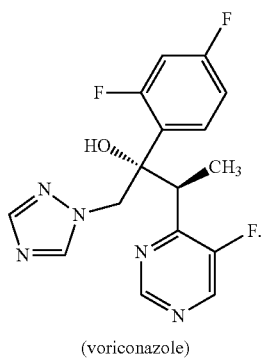

Compound 1

(voriconazole)

Voriconazole is a broad-spectrum triazole antifungal agent for treating the following indications: invasive aspergillosis; severe invasive infection caused by fluconazole-resistant *Candida* spp. (including *Candida krusei*); and severe infection caused by *Scedosporium* spp. and *Fusarium* spp.

It has been reported that there are two main methods for preparing voriconazole. The first method for preparing voriconazole is preparing a (2R,3S/2S,3R) racemate followed by resolution. The second method is preparing voriconazole directly by asymmetric condensation with a chiral reagent (a catalyst or a ligand).

Both methods usually generate a compound 2 of the following formula, i.e., voriconazole condensation substance, which is hydrogenated to obtain voriconazole, or the racemate which is resoluted thereafter to obtain voriconazole.

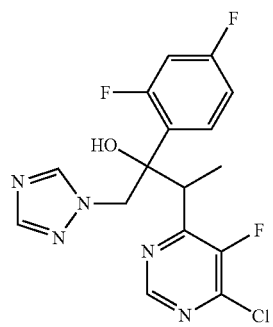

Compound 2

A higher ratio of the amount of 2R,3S/2S,3R enantiomers to the amount of 2R,3R/2S,3S enantiomers of the compound 2 facilitates the further resolution for voriconazole. Various methods for enhancing the ratio of the amount of 2R,3S/2S,3R enantiomers to the amount of 2R,3R/2S,3S enantiomers of the compound 2 are disclosed in the prior art. CN1026788C discloses a method, comprising condensing an intermediate 4-chloro-5-fluoro-6-ethylpyrimidine with 2-(1H-1,2,4-triazole)-2,4-difluoroacetophenone directly under the presence of a strong base, and then separating two enantiomers by a chiral column. However, this method lacks selectivity, involving a low yield with a ratio of the amount of (2R,3S/2S,3R) enantiomers to the amount of (2R,3R/2S,3S) enantiomers of the target compound 2 being only 1:1.1. CN1076019C discloses a method, comprising brominating the intermediate 4-chloro-5-fluoro-6-ethylpyrimidine first, followed by reacting with 2-(1H-1,2,4-triazole)-2,4-difluoroacetophenone through Reformatsky reaction under the presence of excessive zinc, iodine and a small amount of lead as catalysts, so as to directionally generate a relatively large proportion of the 2R,3S/2S,3R enantiomers as required. The conversion and yield in CN1076019C, as directional synthesis technique adopted, are both higher than those of the method comprising separation by chiral column as disclosed in CN1026788C. In addition, the operation of directional synthesis technique is relatively simple. However, the ratio of the amount of (2R,3S/2S,3R) enantiomers to the amount of (2R,3R/2S,3S) enantiomers is merely about 9:1, and thus large quantities of the (2R,3R/2S,3S) enantiomers in the mother liquor still present.

Besides, in the prior art, e.g., CN1919846A and CN103788073A, a method for asymmetrical induction reactions by adding transition metal catalysts and chiral ligand (reagents) during the condensation process is disclosed. However, this method also has the following problems by far. Firstly, transition metal catalysts, which are expensive and difficult to obtain in large quantities, are used in the asymmetric synthesis. Therefore, this method is still in the stage of preparing voriconazole samples in a small scale in the laboratory so far, which cannot meet the requirements of industrial production for cost control. Secondly, due to a problem of selectivity of the asymmetric synthesis, an enhancement of the ratio of the amount of (2R,3S/2S,3R) enantiomers to the amount of (2R,3R/2S,3S) enantiomers is limited. the products still comprise a certain proportion of isomer impurities, and thus a resolution in the final and subsequent purification process is still needed.

In conclusion, in case of preparing voriconazole or its intermediate compound 2 on the basis of the methods as disclosed in the prior art, though some of the parameters can be optimized, the utilization rate of starting materials and auxiliary materials still can not be greatly improved in the industrial production process due to limitations of theory and mass production on cost control. There is a need to develop a new technical solution for preparing voriconazole bulk drug with a higher yield and a lower production cost. Such technical solution can increase the utilization rate of starting materials and auxiliary materials for preparing voriconazole, thereby reducing the waste of resources and protecting the environment, minimizing the production cost, and promoting large-scale industrial production.

SUMMARY OF THE INVENTION

The present invention provides a method for preparing voriconazole and an intermediate thereof by using a voriconazole condensate isomer. The method has the advantages of simple reaction conditions and simultaneous recovery of two raw materials. Therefore, it is very suitable for large-scale industrial recycling production.

In the inventive method, a mother liquor for preparing voriconazole condensate is recycled, which can improve the utilization rate of starting materials and auxiliary materials for preparing voriconazole, reduce the waste of resources and protect the environment, thereby minimizing the production cost.

The invention provides a method for preparing an intermediate of voriconazole, comprising: using the voriconazole condensate isomer, i.e., the compound 2, or a salt thereof, as a raw material, which is reacted under an acidic condition and post-treated to obtain a compound 3 and a compound 4. The specific reaction scheme is as follows:

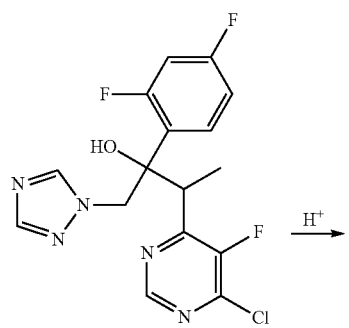

Compound 2 wherein the compound 2 is a substance with a configuration of 2S,3S or 2R,3R or 2S,3R or 2R,3S in two chiral centers, or a mixture of two or more of the above substances. Preferably, the compound 2 is mainly a mixture of enantiomers having a configuration of 2S,3S/2R,3R, and may also comprise a mixture of enantiomers having a configuration of 2R,3S/2S,3R. More preferably, the compound 2 is mainly derived from the mother liquor used for the preparation of voriconazole condensate.

In one embodiment of the invention, the acidic condition refers to an acidic aqueous solution or a mixture of an acidic aqueous solution and an organic solvent.

In another embodiment of the invention, an acid in the acidic aqueous solution is selected from the group consisting of hydrochloric acid, sulfuric acid, trifluoroacetic acid, acetic acid, nitric acid and phosphoric acid.

In another embodiment of the invention, the concentration of the acidic aqueous solution ranges from 2 mol/L to 5 mol/L.

In one embodiment of the invention, a molar ratio of the compound 2 or the salt thereof to the acid ranges from 1:2 to 1:20, preferably from 1:5 to 1:10.

In another embodiment of the invention, the organic solvent is selected from the group consisting of hydrocarbon, halogenated hydrocarbon, ester, ketone or ether, or a combination thereof; wherein hydrocarbon or halogenated hydrocarbon is preferably selected from the group consisting of dichloromethane, toluene and cyclohexane; wherein ether is preferably selected from the group consisting of isopropyl ether, methyl tert-butyl ether, dioxane and tetrahydrofuran; ketone is preferably acetone or butanone; and ester is preferably selected from the group consisting of ethyl acetate, isopropyl acetate and methyl acetate.

In one embodiment of the invention, the ratio of an amount of the compound 2 or the salt thereof in mol to a volume of the organic solvent in ml is in the range of 5-15 mol/ml, preferably 5-10 mol/ml.

In another embodiment of the invention, the reaction temperature ranges from 40° C. to 90° C.

In one embodiment of the invention, the reaction time ranges from 2-12 hours, preferably 5-10 hours.

In addition, the present invention also provides a method for preparing voriconazole, comprising the following steps: preparing a compound 3 and a compound 4 in accordance with the above method, using the compound 3 and the compound 4 thus obtained as raw materials, brominating the compound 3 first, followed by condensing with the compound 4 to obtain the compound 2' having a configuration of 2S,3R/2R,3S, then hydrogenating, resolving and refining the compound 2' to obtain voriconazole. The specific reaction scheme is as follows:

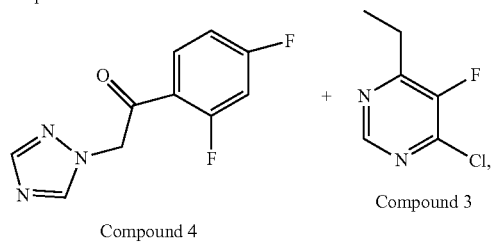

Compound 3 Compound 4

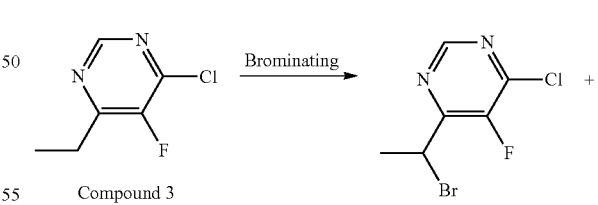

Compound 3 Compound 5

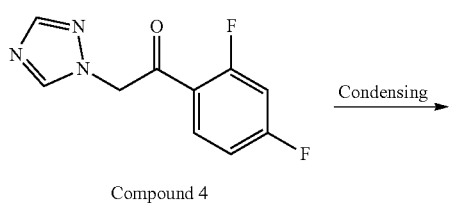

Compound 4

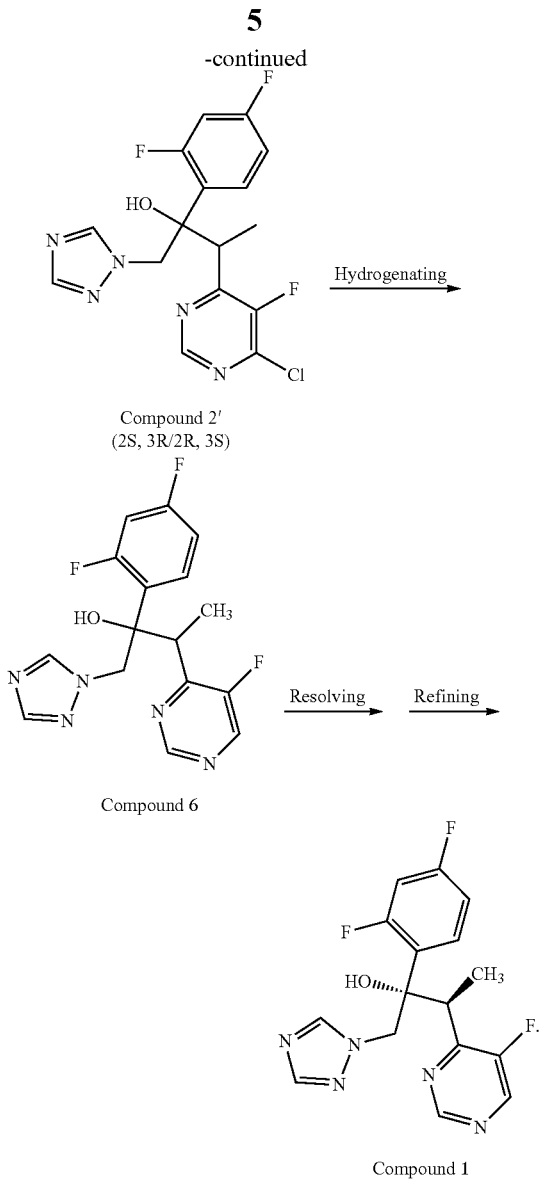

The specific method for preparing voriconazole from the compound 3 and the compound 4 can be referred to the examples in this specification or the prior art, e.g. CN1076019C.

Compared with the prior art, the advantages of the method of the invention are as follows:

(1) The starting material, the compound 2, used in the inventive method is mainly a solid waste or impurity produced in the process of preparing the compound 2' in the prior art. Therefore, the method of the invention is a clean production method of "making waste profitable". The method of the invention can significantly increase the utilization rate of starting materials and auxiliary materials for preparing voriconazole over that in the prior art, save resources and protect the environment, in which not only the production cost is minimized, but also the production of voriconazole is recyclable.

(2) Two substances, the compound 3 and the compound 4, can be prepared by the method of the invention by adopting simple reaction conditions. Compared with the method for preparing the compound 3 and the compound 4 in the prior art, the method of the invention has the advantages including less synthesis steps, a high yield, low cost and easy large-scale industrial production.

DETAILED DESCRIPTION OF THE INVENTION

The following examples are used to further illustrate the present invention. These examples exemplarily illustrate a method of preparing voriconazole and intermediate thereof in accordance with the present invention, which are only intended to illustrate the invention without limiting the scope of the invention in any aspects.

Example 1

Preparation of 4-chloro-6-ethyl-5-fluoropyrimidine and 2',4'-difluoro-2-[1-(1H-1,2,4-triazolyl)]acetophenone 38.3 g of the compound 2 (with a major configuration of 2S,3S/2R,3R, and a minor configuration of 2R,3S/2S,3R) was added to a flask with 500 ml of 1 mol/L diluted hydrochloric acid, heated to 60-70° C. and reacted for 6-7 hours. After the reaction was completed, it was cooled to 0° C., adjusted to a pH value of 7-8 with sodium hydroxide aqueous solution, and extracted with dichloromethane to obtain a mixed liquor of the compound 3 and the compound 4. The mixed liquor was subjected to reduced pressure distillation to obtain 22 g of a solid residue, i.e., the compound 4, with a purity of 92% and a yield of 98.7%. The distilled fraction was subjected to atmospheric distillation to evaporate the solvent dichloromethane, and then subjected to reduced pressure distillation to obtain a 14.2 g of a distillate, i.e., the compound 3, with a purity of 99.1% and a yield of 88.4%.

Example 2

Preparation of 4-chloro-6-ethyl-5-fluoropyrimidine and 2',4'-difluoro-2-[1-(1H-1,2,4-triazolyl)]acetophenone 38.3 g of the compound 2 (with a major configuration of 2S,3S/2R,3R, and a minor configuration of 2R,3S/2S,3R) was added to a flask with 380 ml of 3 mol/L sulfuric acid, heated to 40-50° C. and reacted for 10 hours. After the reaction was completed, it was cooled to room temperature, adjusted to a pH value of 7-8 with sodium hydroxide aqueous solution, and extracted with ethyl acetate to obtain a mixed liquor of the compound 3 and the compound 4. The mixed liquor was subjected to reduced pressure distillation to obtain 21 g of a solid residue, i.e., the compound 4, with a purity of 90% and a yield of 94.2%. The distilled fraction was subjected to atmospheric distillation to evaporate the solvent ethyl acetate, and then subjected to reduced pressure distillation to obtain a 13.6 g of a distillate, i.e., the compound 3, with a purity of 99.0% and a yield of 84.6%.

Example 3

Preparation of 4-chloro-6-ethyl-5-fluoropyrimidine and 2',4'-difluoro-2-[1-(1H-1,2,4-triazolyl)]acetophenone 38.3 g of the compound 2 (with a major configuration of 2S,3S/2R,3R, and a minor configuration of 2R,3S/2S,3R), 380 ml of dioxane and 11.5 g of trifluoroacetic acid were added to a flask, heated to 70-90° C. and reacted for 3-5 hours. After the reaction was completed, it was cooled to room temperature, adjusted to a pH value of 7-8 with an sodium hydroxide aqueous solution, and extracted with dichloromethane to obtain a mixed liquor of the compound 3 and the compound 4. The mixed liquor was subjected to reduced pressure distillation to obtain 20 g of a solid residue, i.e., the compound 4, with a purity of 91% and a yield of 89.6%. The distilled fraction was subjected to atmospheric distillation to evaporate the solvent dichloromethane, and then subjected to reduced pressure distillation to obtain a 13.7 g of a distillate, i.e., the compound 3, with a purity of 99.3% and a yield of 85.3%.

Example 4

Preparation of (2R,3S)-2-(2,4-difluorophenyl)-3-(5-fluoro-4-pyrimidyl)-1-(1H-1,2,4-triazol-1-yl)-2-butanol 38.3 g of the compound 2 (with a major configuration of 2S,3S/2R,3R, and a minor configuration of 2R,3S/2S,3R), 190 ml of dioxane, 190 ml of water and 50 ml of concentrated hydrochloric acid were added to a flask, heated to 50-70° C. and reacted for 5-7 hours. After the reaction was completed, it was cooled to room temperature, adjusted to a pH value of 7-8 with an sodium hydroxide aqueous solution, and extracted with dichloromethane to obtain a mixed liquor of the compound 3 and the compound 4. The mixed liquor was subjected to reduced pressure distillation to obtain a solid residue, i.e., the compound 4. The distilled fraction was subjected to atmospheric distillation to evaporate the solvent dichloromethane, and then subjected to reduced pressure distillation to obtain a distillate, i.e., the compound 3. The compound 3 was brominated, then reacted with the compound 4 through Reformatsky condensation reaction under the presence of zinc powder and zinc chloride, hydrogenated and dechlorinated under the presence of Pd/H₂, followed by chiral resolution and refining to obtain 8.7 g of 2-(2,4-difluorophenyl)-3-(5-fluoro-4-pyrimidyl)-1-(1H-1,2,4-triazol-1-yl) butan-2-ol (i.e., voriconazole), with a purity of 99.5% and a yield of 24%.

The invention claimed is:

1. A method for preparing voriconazole intermediate, comprising the following steps: reacting a compound 2 or a salt thereof as a starting material under an acidic condition and subjecting to a post-treatment to obtain a compound 3 and a compound 4:

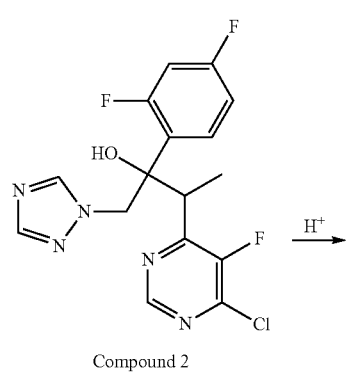

Compound 2

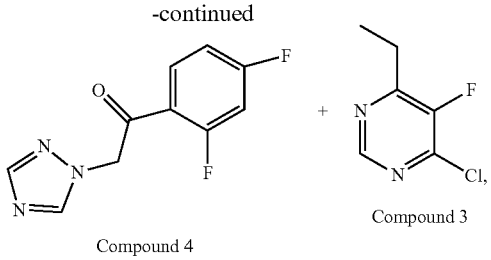

Compound 4

Compound 3 wherein the compound 2 is a substance with a configuration of 2S,3S or 2R,3R or 2S,3R or 2R,3S in two chiral centers, or a mixture of two or more of the above substances.

2. The method according to claim 1, wherein the acidic condition refers to an acidic aqueous solution or a mixture of an acidic aqueous solution and an organic solvent.

3. The method according to claim 2, wherein the acidic aqueous solution is selected from the group consisting of an aqueous solution of hydrochloric acid, an aqueous solution of sulfuric acid, an aqueous solution of trifluoroacetic acid, an aqueous solution of acetic acid, an aqueous solution of nitric acid and an aqueous solution of phosphoric acid.

4. The method according to claim 1, wherein a molar ratio of the compound 2 or the salt thereof to an acid for producing the acidic condition ranges from 1:2 to 1:20.

5. The method according to claim 2, wherein the organic solvent is selected from the group consisting of hydrocarbon or halogenated hydrocarbon, ester, ketone and ether, or a combination thereof.

6. The method according to claim 2, wherein a ratio of an amount of the compound 2 or the salt thereof in mol to a volume of the organic solvent in ml is 5-15 mol/ml.

7. The method according to claim 1, wherein the reaction is performed at a temperature from 40° C. to 90° C.

8. The method according to claim 1, wherein the reaction is performed for 2-12 hours.

9. A method for preparing voriconazole, comprising the following steps: preparing the compound 3 and the compound 4 with the method according to any one of claims 1-8, using the compound 3 and the compound 4 thus obtained as starting materials, brominating the compound 3, followed by condensing with the compound 4 to obtain a compound 2' having a configuration of 2S,3R/2R,3S, then hydrogenating, resolving and refining the compound 2' to obtain voriconazole; wherein the synthesis scheme is as follows:

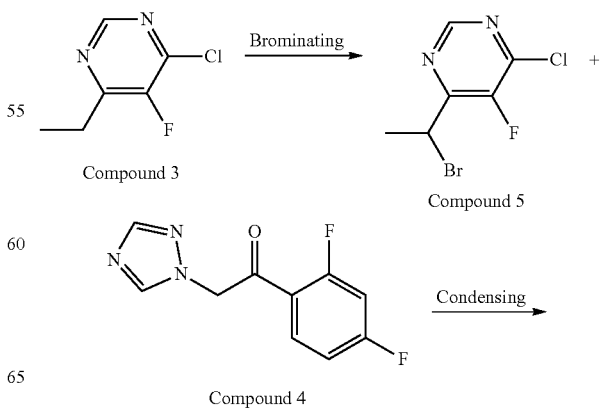

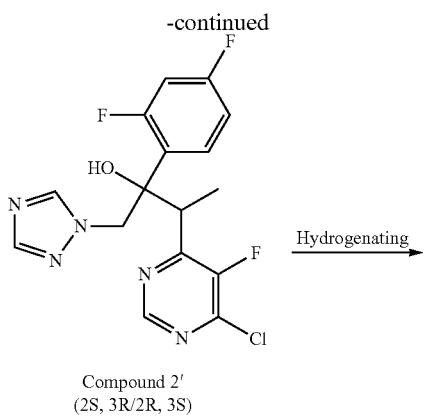

Compound 2'
(2S, 3R/2R, 3S)

Hydrogenating →

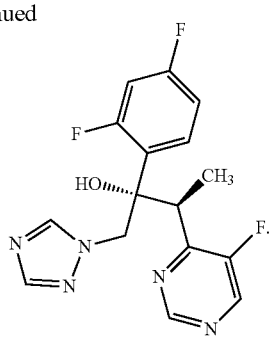

Compound 1

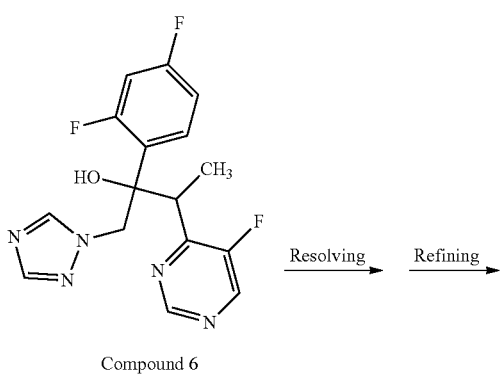

Compound 6

Resolving → Refining →

10. The method according to claim 1, wherein the compound 2 is a mixture of enantiomers having a configuration of 2S,3S/2R,3R.

11. The method according to claim 1, wherein the compound 2 is derived from a mother liquor during the preparation of voriconazole condensate.

12. The method according to claim 4, wherein the molar ratio of the compound 2 or the salt thereof to the acid for producing the acidic condition ranges from 1:5 to 1:10.

13. The method according to claim 5, wherein hydrocarbon or halogenated hydrocarbon is selected from the group consisting of dichloromethane, toluene and cyclohexane; ether is selected from the group consisting of isopropyl ether, methyl tert-butyl ether, dioxane and tetrahydrofuran; ketone is acetone or butanone; and ester is selected from the group consisting of ethyl acetate, isopropyl acetate and methyl acetate.

14. The method according to claim 6, wherein the ratio of the amount of the compound 2 or the salt thereof in mol to the volume of the organic solvent in ml is 5-10 mol/ml.

15. The method according to claim 8, wherein the reaction is performed for 5-10 hours.

\* \* \* \* \*